(12) United States Patent
Barnes

(10) Patent No.: US 11,571,196 B2
(45) Date of Patent: *Feb. 7, 2023

(54) SURGICAL SYSTEM

(71) Applicant: Life Spine, Inc., Huntley, IL (US)

(72) Inventor: Bryan Barnes, Athens, GA (US)

(73) Assignee: Life Spine, Inc., Huntley, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/532,832

(22) Filed: Nov. 22, 2021

(65) Prior Publication Data

US 2022/0079572 A1 Mar. 17, 2022

Related U.S. Application Data

(63) Continuation of application No. 16/329,189, filed as application No. PCT/US2017/049135 on Aug. 29, 2017, now Pat. No. 11,179,144.

(Continued)

(51) Int. Cl.
*A61B 17/17* (2006.01)
*A61B 17/00* (2006.01)
(Continued)

(52) U.S. Cl.
CPC .... *A61B 17/00234* (2013.01); *A61B 17/1757* (2013.01); *A61B 17/3423* (2013.01);
(Continued)

(58) Field of Classification Search
CPC ............ A61B 17/1757; A61B 17/1739; A61B 2017/3455; A61B 2017/347;
(Continued)

(56) References Cited

U.S. PATENT DOCUMENTS 6,793,656 B1 * 9/2004 Mathews ............... A61F 2/4455
606/279
7,175,631 B2 2/2007 Wilson et al.
(Continued)

FOREIGN PATENT DOCUMENTS

CN 1909845 A 2/2007

OTHER PUBLICATIONS

EPO Search Report for Application No. EP 17847374.0 dated Jul. 10, 2020, 10 pages.
(Continued)

*Primary Examiner* — Anu Ramana
(74) *Attorney, Agent, or Firm* — Foley & Lardner LLP

(57) ABSTRACT

A surgical system includes an instrument portal comprising a first proximal end, a first distal end, and a first elongated member, the first elongated member comprising a first bore defining a first diameter, wherein the first bore extends from the first distal end to the first proximal end, wherein the maximum clearance of the instrument portal is the first diameter, and a drill guide reducer configured to be inserted into the instrument portal, the drill guide reducer comprising an elongated cylindrical member defining an outside diameter such that the drill guide reducer is sized to fit within the instrument portal and defining an inner diameter configured to receive a drill guide, wherein the inner diameter of the drill guide reducer is smaller than the first diameter of the instrument portal.

14 Claims, 6 Drawing Sheets

Related U.S. Application Data

(60) Provisional application No. 62/380,671, filed on Aug. 29, 2016.

(51) Int. Cl.
*A61B 17/70* (2006.01)
*A61B 17/80* (2006.01)
*A61B 17/34* (2006.01)
*A61B 17/90* (2006.01)
*A61B 90/00* (2016.01)

(52) U.S. Cl.
CPC ............ *A61B 17/70* (2013.01); *A61B 17/708* (2013.01); *A61B 17/7074* (2013.01); *A61B 17/7082* (2013.01); *A61B 17/80* (2013.01); *A61B 17/90* (2021.08); *A61B 2017/0042* (2013.01); *A61B 2017/0092* (2013.01); *A61B 2090/3966* (2016.02)

(58) Field of Classification Search
CPC ........ A61B 2017/3488; A61B 17/7074; A61B 17/7076; A61B 17/7079
See application file for complete search history.

(56) References Cited

U.S. PATENT DOCUMENTS

| | | | |
|---|---|---|---|
| 7,357,804 B2 | 4/2008 | Binder et al. | |
| 8,308,777 B2* | 11/2012 | Assell | A61B 17/1757 606/279 |
| 8,540,719 B2 | 9/2013 | Peukert et al. | |
| 8,641,717 B2* | 2/2014 | Defossez | A61M 25/09041 606/86 R |
| 9,204,906 B2 | 12/2015 | Cannestra | |
| 9,795,771 B2* | 10/2017 | Trieu | A61M 29/02 |
| 2004/0143265 A1* | 7/2004 | Landry | A61B 17/701 606/279 |
| 2006/0189997 A1 | 8/2006 | Guenther et al. | |
| 2007/0142855 A1* | 6/2007 | Koysh | A61B 17/3421 606/191 |
| 2010/0023065 A1* | 1/2010 | Welch | A61B 17/3472 606/86 R |
| 2010/0094305 A1* | 4/2010 | Chang | A61B 17/7004 606/90 |
| 2010/0114179 A1* | 5/2010 | Moore | A61B 17/7085 606/86 A |
| 2010/0185245 A1* | 7/2010 | Paul | A61B 17/7071 606/301 |
| 2010/0191066 A1* | 7/2010 | Koysh | A61B 17/3421 606/191 |
| 2010/0262200 A1 | 10/2010 | Ray et al. | |
| 2010/0318134 A1* | 12/2010 | Roche | A61F 2/441 606/86 R |
| 2012/0022597 A1 | 1/2012 | Gephart et al. | |
| 2012/0253316 A1 | 10/2012 | Oktavec et al. | |
| 2012/0277864 A1 | 11/2012 | Brodke et al. | |
| 2013/0103036 A1 | 4/2013 | McGhie | |
| 2015/0327874 A1 | 11/2015 | McBride | |
| 2016/0038195 A1 | 2/2016 | Genovese et al. | |
| 2016/0143742 A1 | 5/2016 | Asfora | |
| 2016/0220278 A1 | 8/2016 | Yue | |

OTHER PUBLICATIONS

International Search Report and Written Opinion on PCT/US2017/049135 dated Nov. 2, 2017.

* cited by examiner

SURGICAL SYSTEM

CROSS REFERENCE TO RELATED APPLICATION

This Application is a continuation of U.S. patent application Ser. No. 16/329,189, filed Feb. 27, 2019, which is a U.S. National Phase Application under 35 U.S.C. § 371 of International Application No. PCT/US2017/049135, filed on Aug. 29, 2017, which claims priority to U.S. Provisional Patent Application No. 62/380,671, filed Aug. 29, 2016, the contents of which are hereby incorporated herein by reference in their entireties.

TECHNICAL FIELD

This disclosure relates to minimally invasive spinal surgery, and more particularly to devices for securing a pedicle screw or lateral mass screw to a vertebral lateral mass or to a thoracic or lumbar pedicle.

BACKGROUND

The spine includes a plurality of vertebrae arranged in a vertical column. Traditionally, implant devices have been used to secure bone or bone segments to promote the healing and repair of various parts of the human body. Between each vertebra there is an intervertebral disc that provides a cushion between adjacent vertebrae and transmits force between adjacent vertebrae. Traditionally, degenerative disc disease has been treated by surgically removing a diseased disc and interesting an implant in the space vacated by the diseased disc. The implant may be bone or other biocompatible implants. The adjacent vertebrae are then immobilized relative to one another using pedicle screw or lateral mass screw fixation. Subsequently, the adjacent vertebrae grow into one solid piece of bone over time. This process can include using a bone graft or bone graft substitute to stabilize the vertebrae.

Conventionally, spinal rods that immobilize vertebral bones are typically anchored to the vertebrae through bone screws that extend through the pedicle or lateral mass into vertebral bodies or bones by hooks that engage around the vertebrae. Spinal rods have been used, by connecting to the screws or anchor members by coupling members. While incisions are required during many surgical procedures to gain access to the site, such incisions can cause injury to the patients' body. To avoid unnecessary damage, small incisions are often preferred.

Many traditional approaches require the use of guidewires to set a pedicle screws or lateral mass screws to a vertebral body prior to using some minimally invasive surgical (MIS) system to anchor the screw to the mass and perform a surgery. In one traditional approach, the MIS system uses at least two pedicle anchors or screws, in which the screws are secured to the vertebrae by sliding the MIS device down a guidewire, like the MIS implant device described in U.S. Patent App. No. 2012/0022597. As described therein, the procedure includes a surgeon inserting a Jamshidi needle percutaneously over the posterior spinal anatomy thereby creating a small incision. The Jamshidi needle is able to hold the guidewire and is used to percutaneously force the guidewire into place. It is only after the guidewire is secured that a docking device is used to secure an anchor to a vertebral mass. Traditionally this is done by sliding the docking device down the guidewire toward the pre-positioned guidewire path.

Thus, a need exists for a MIS system that can secure a pedicle screw or lateral mass screw to a vertebral mass of a patient by anchoring itself to a vertebral mass without specifically requiring assistance by a guidewire. Moreover, a need exists for a hand held device that includes an instrument portal for receiving a variety of instruments during a surgery and/or includes a docking mechanism to secure a screw, such as a polyaxial screw, to a vertebral lateral mass or pedicle.

SUMMARY

Provided are systems, apparatuses, and methods for securing a pedicle screw or lateral mass screw to a vertebral lateral mass or pedicle during minimally invasive spinal surgery.

In an embodiment, an example system includes a minimally invasive surgical apparatus having an instrument portal, an anchor pin receiving chamber, and a handle. The instrument portal may comprise an instrument portal comprising a first proximal end, a first distal end, and a first elongated member. The first elongated member may include a first cylindrical bore having a first diameter. The first cylindrical bore may extend from the first distal end to the first proximal end.

The anchor pin receiving chamber may be fixed in parallel to the instrument portal. The anchor pin receiving chamber may include a second proximal end, a second distal end, and a second elongated member comprising a second cylindrical bore. The second cylindrical bore may extend from the second distal end to the second proximal end. The second diameter may be smaller than the first diameter. The handle may depend from a surface of the instrument portal or a surface of the anchor pin receiving chamber.

In certain example embodiments, the system and/or apparatus further includes at least one or more of the following devices: an inner cannula, an anchoring pin, a drill guide reducer, a drill guide, or a pedicle screw or lateral mass screw reducer.

The details of one or more embodiments of the disclosure are set forth in the accompanying drawings and the description below. Other features, objects, and advantages of the disclosure will be apparent from the description, drawings, and from the claims

BRIEF DESCRIPTION OF DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Figure 1:
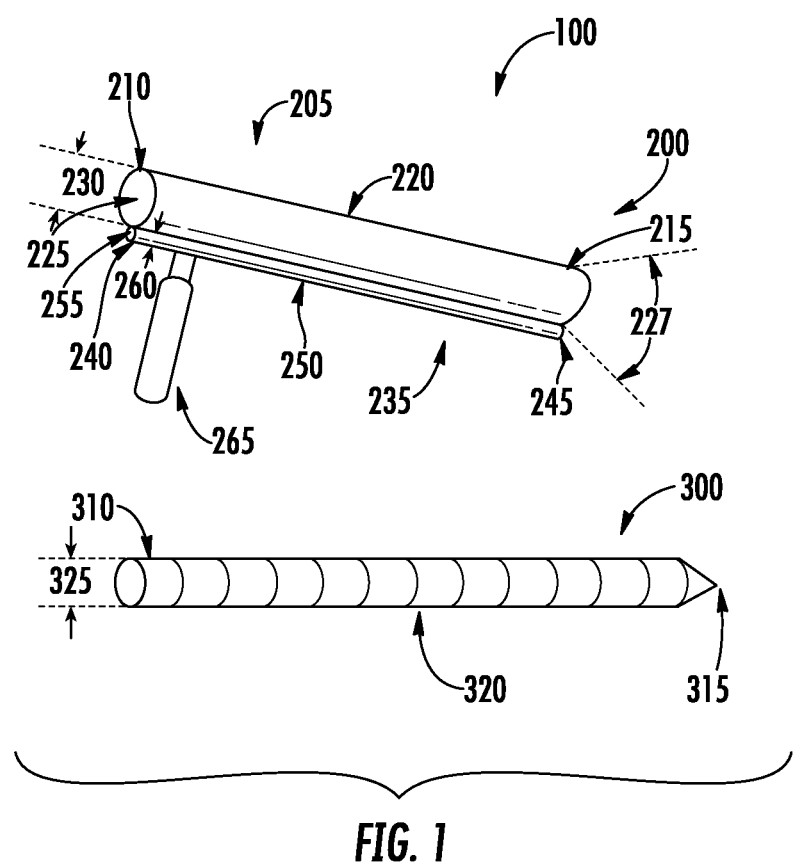
FIG. 1 is a perspective view of a MIS system that includes a MIS apparatus and an inner cannula in accordance with the present disclosure.

The following is a description of several illustrations of spinal fixation devices and methods for treating spinal injuries and abnormalities.

Certain terminology is used herein for convenience only and is not to be taken as a limitation on the present invention. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

FIG. 1 illustrates an example of a minimally invasive surgical (MIS) system 100 that includes a MIS apparatus 200 for securing a pedicle screw or lateral mass screw to a vertebral lateral mass 900 in accordance with the present disclosure (FIGS. 13-16 depict the vertebral lateral mass 900). The MIS system 100 has the ability to anchor itself to a lateral vertebral mass 900 and secure a screw to the lateral vertebral mass or vertebral pedicle without needing the use of a guidewire. In many embodiments, the MIS apparatus 200 includes an instrument portal 205, an anchor pin receiving chamber 235, and a handle 265. As described in detail below, the instrument portal 205 is sized to receive various surgical instruments, in some embodiments the instrument portal receives various diameter reducers for example to meet the requirements of various surgical scenarios. In general, the MIS apparatus 200 can be secured to a vertebral lateral mass or vertebral pedicle via inserting a fastener into the anchor pin receiving chamber 235, and once secured, a screw can be inserted into the vertebral lateral mass or pedicle 900 via the instrument portal 205 and then the MIS apparatus 200 can be withdrawn and the screw left within the body. Various suitable types of screws can be used with the MIS system 200. Suitable types of screws can include, for example, cervical lateral mass screws, such as posterior cervical lateral mass screws, and thoracic and lumbar pedicle screws. In several embodiments described herein, the screw is described as a polyaxial pedicle screw or lateral mass screw, but the invention is not specifically limited to such embodiments. One example of a suitable polyaxial screw can be the DENALI® Mini Polyaxial Screw having a circumference of 3.5 millimeters and a length of 14 millimeters, which is sold by K2M Inc. Suitable screws can also have a variety of suitable screw head configurations, shapes, and sizes. For example, the screw can have a U-shaped or tulip shaped head. In certain embodiments the screws described herein can include one or more guidewires connected to the head of the screw, the guidewires being used to secure a rod to the screw 800 after the screw 800 has been fixed to a vertebral mass. Other suitable screws as known to those having skill in the art can be use as well.

In the example MIS apparatus 200 shown in FIG. 1, the instrument portal 205 of the MIS apparatus 200 includes a first proximal end 210, a first distal end 215, and a first elongated member 220. The first elongated member 220 includes a first cylindrical bore 225 having a first diameter 230. The first cylindrical bore 225 can be used to receive a variety of different tools, instruments, accessories, and/or devices for performing a MIS surgery. For example, the first cylindrical bore 225 can receive various types of surgical instruments, for example, the first cylindrical bore 255 can receive any of the following instruments described in further detail below: an inner cannula 300, a drill guide reducer 500, a drill guide 600, a pedicle screw or lateral mass screw reducer 700, and/or a pedicle screw or lateral mass screw 800. In certain embodiments, the first diameter 230 of the first cylindrical bore 225 is about 12 millimeters, but as described below this working diameter can essentially be changed through the introduction of various types of reducers, like the drill guide reducer 500 or the pedicle screw or lateral mass screw reducer 700 described below. The first cylindrical bore 225 can extend a distance from the first distal end 215 to the first proximal end 210. In certain embodiments this distance traverses the entire first elongated member 220, but in certain embodiments the distance traversed need not be continuously connected nor encompass the entire length of the first elongated member 220. Moreover, in certain embodiments the first diameter 230 may vary as it traverses the first elongated member 220.

In certain embodiments, the instrument portal 205 can be radiolucent so that the position of instruments situated within the instrument portal 205 can be accurately ascertained during surgery. One such way of ascertaining the position of instruments is via an X-ray machine. In certain embodiments, the first distal end 215 of the instrument portal 205 comprises an oblique end that is contoured to fit against the lateral mass 900. This allows for easier insertion of a polyaxial screw into a lateral vertebral mass. In certain embodiments the oblique end can form an angle 227 of about 45 degrees.

In the example MIS apparatus 200 shown in FIG. 1, the anchor pin receiving chamber 235 of the MIS apparatus 200 includes a second proximal end 240, a second distal end 245, and a second elongated member 250. The second elongated member 250 includes a second cylindrical bore 255 having a second diameter 260. In certain embodiments the second diameter 260 of the second cylindrical bore 255 is smaller than the first diameter 230 of the first cylindrical bore 225. In certain embodiments the second diameter 260 can range from about 1 millimeter to about 6 millimeters. In certain embodiments, the second diameter is about 2 millimeters. The second cylindrical bore 255 can extend a distance from the second distal end 245 to the second proximal end 240. In certain embodiments this distance traverses the entire second elongated member 250, but in certain embodiments the distance traversed need not be continuously connected nor encompass the entire length of the second elongated member 250. Moreover, in certain embodiments the second diameter 260 may vary as it traverses the second elongated member 250.

FIG. 1 shows the anchor pin receiving chamber 235 as being fixed in parallel to the instrument portal 205. The anchor pin receiving chamber 235 can be fixed to the MIS apparatus 200 in a variety of suitable ways. For example, the fixture can be a permanent fixture such as an adhesive, glue, welding joint, or other suitable long-lasting and/or permanent fastener. The fixture can also be created by integrally molding the anchor pin receiving chamber 235 and the instrument portal 205 together. In such integral molding, the anchor pin receiving chamber 235 and the instrument portal 205 can comprise two parts of a larger frame. For example, the anchor pin receiving chamber 235 and the instrument portal 205 can be two barrels of a larger solid structure. The outer surfaces of the pin receiving chamber 235 and the instrument portal 205 need not me cylindrical in several of the embodiments herein. The fixture can also be created through the use of a releasably coupleable fastener, like a zipper, clamp, bracket, or clip. Other suitable means for fixing can be used as known to those having ordinarily skill in the art. Although the figures show the MIS apparatus 200 as comprising a single anchor pin receiving chamber 235, it should be understood that other numbers of anchor pin receiving chambers 235 and/or other numbers of anchor pins can be included in the MIS apparatus 200. For example, in certain embodiments two or more anchor pin receiving chambers 235 are fixed to a single instrument receiving chamber 205.

In the example MIS apparatus 200 shown in FIG. 1, the MIS apparatus 200 includes a handle 265 depending from a surface of the anchor pin receiving chamber 235. In certain embodiments the handle depends from another surface such as a surface of the instrument portal 205. In embodiments where the anchor pin receiving chamber 235 and the instrument portal 205 are integrally formed, the handle 265 can be fixed to a surface of the integrally formed structure. The handle 265 is designed for gripping of the MIS apparatus 200. In certain embodiments the handle 265 includes various grooves or indents to receive corresponding fingers. The handle 265 can take the form of various suitable shapes. Some suitable types of shapes include cubes, rectangular prisms, and cylinders. Other suitable shapes and configurations for the handle 265 can be used as known to those having skill in the art.

Figure 2:
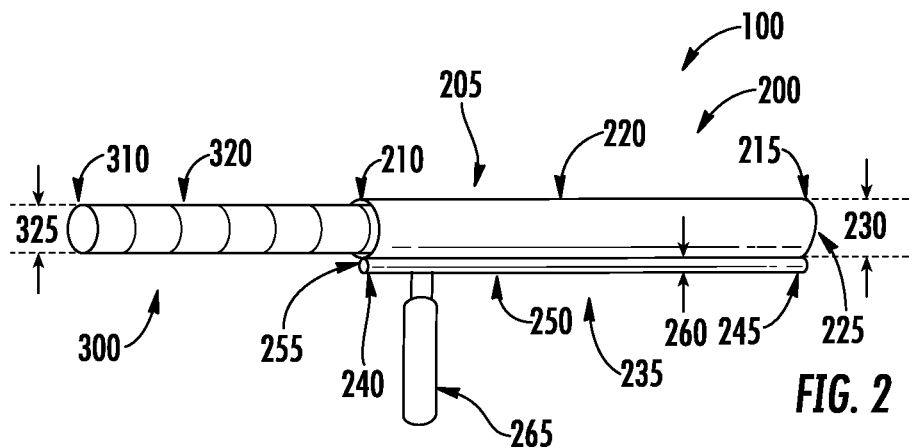
FIG. 2 is another perspective view of a MIS system that includes a MIS apparatus and an inner cannula in accordance with the present disclosure.
Figure 3:
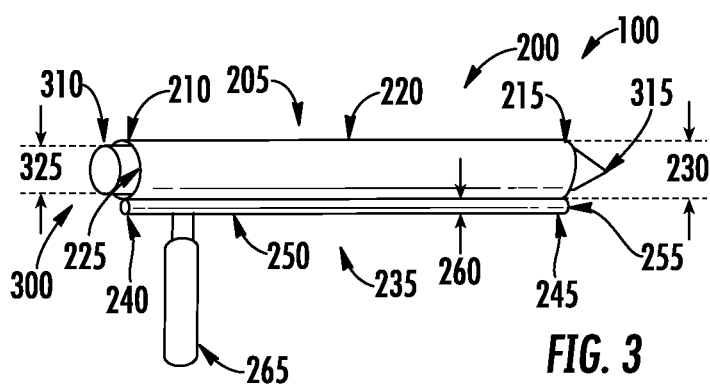
FIG. 3 is another perspective view of a MIS system that includes a MIS apparatus and an inner cannula in accordance with the present disclosure.

In certain embodiments, the MIS system 100 includes an inner cannula 300, which can be inserted into the instrument portal 205 of the MIS apparatus 200 for dilating, cutting, and/or stretching bodily tissue and/or bone when advancing the MIS apparatus 200 toward a lateral mass 900. FIGS. 2-3 illustrate one such embodiment. The inner cannula 300 includes a proximal end 310, a distal end 315, and an elongated member 320 having an outer diameter 325 sized to fit within the instrument portal 205. In certain embodiments the outer diameter 325 of the inner cannula 300 is sized to fit against the first diameter of the first cylindrical bore 225. In certain embodiments the distal end 315 of the inner cannula 300 is tapered, which can act as a wedge to assist in the traversal of the MIS apparatus 200 toward the lateral mass 900. In certain embodiments, the inner cannula 300 include an inner bore (not shown) that traverses the length of the elongated member 320 so that fluid and body tissue can be sucked out or withdrawn from the body as the MIS apparatus 200 traverses toward the vertebral lateral mass 900. In certain embodiments the tapered distal end 315 is conical and/or wedge shaped. In certain embodiments a surface of the elongated member 320 can include threads, grips, or other means for creating a friction fit between the elongated member 320 and the first cylindrical bore 225.

In certain embodiments the inner cannula 300 is radiopaque so that the position of inner cannula 300 can be seen by an X-ray machine when it's within the instrument portal 205. In such embodiments, the instrument portal 205 can be radiolucent.

Figure 4:
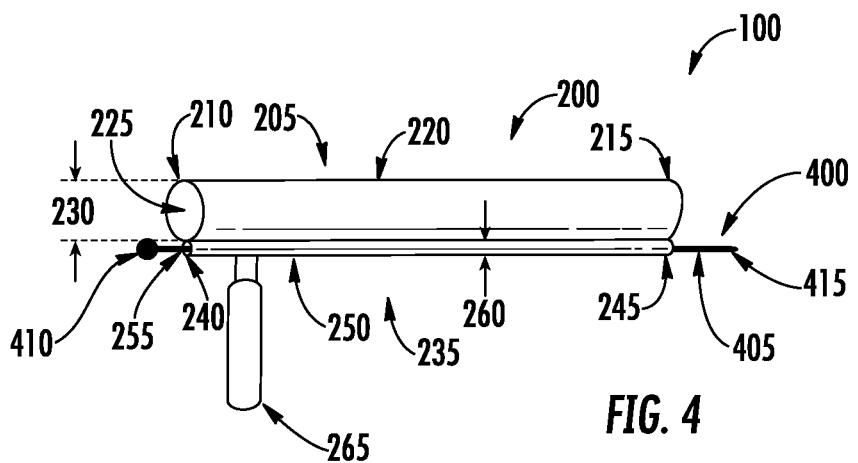
FIG. 4 is a perspective view of a MIS system that includes a MIS apparatus and an anchor pin in accordance with the present disclosure.
Figure 5:
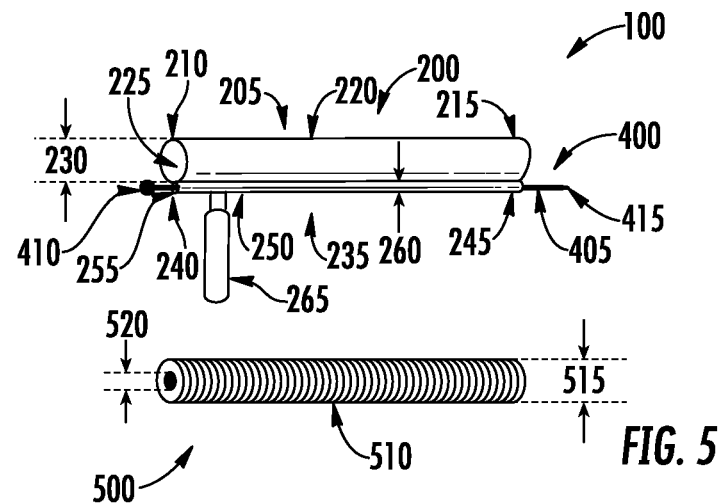
FIG. 5 is a perspective view of a MIS system that includes a MIS apparatus, an anchor pin, and a drill guide reducer in accordance with the present disclosure.
Figure 6:
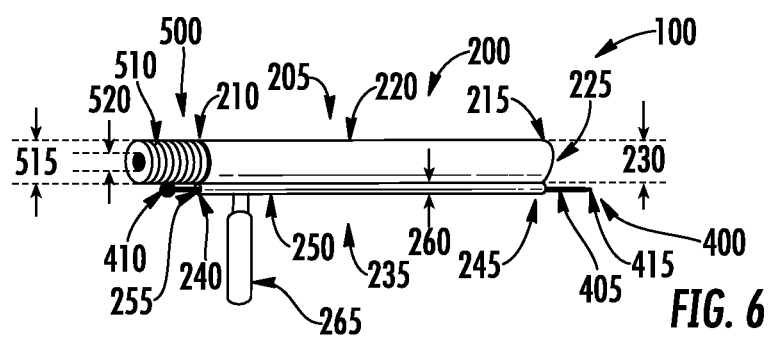
FIG. 6 is another perspective view of a MIS system that includes a MIS apparatus, an anchor pin, and a drill guide reducer in accordance with the present disclosure.
Figure 7:
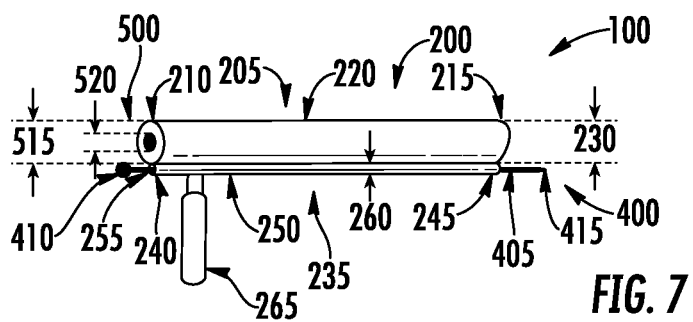
FIG. 7 is another perspective view of a MIS system that includes a MIS apparatus, an anchor pin, and a drill guide reducer in accordance with the present disclosure.
Figure 8:
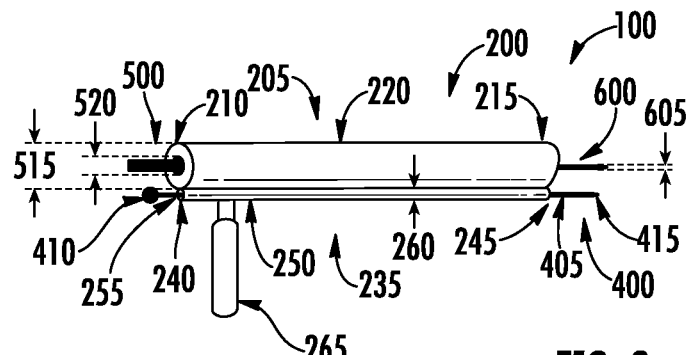
FIG. 8 is a perspective view of an example MIS system that includes a MIS apparatus, an anchor pin, a drill guide reducer, and a drill guide.
Figure 9:
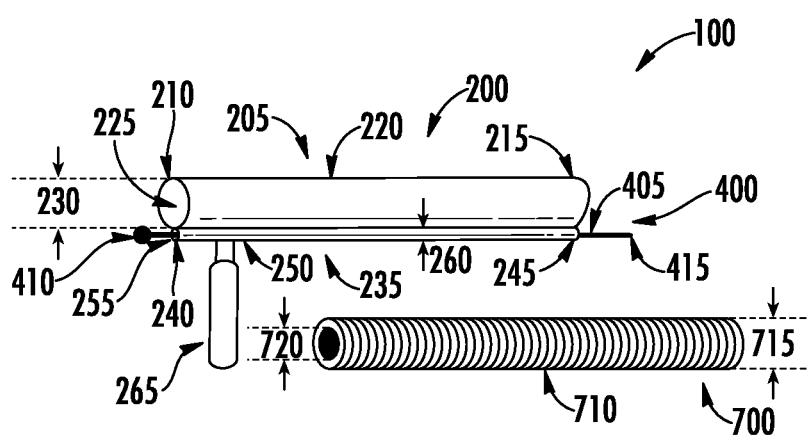
FIG. 9 is a perspective view of an example MIS system that includes a MIS apparatus, an anchor pin, and a pedicle screw or lateral mass screw reducer.
Figure 10:
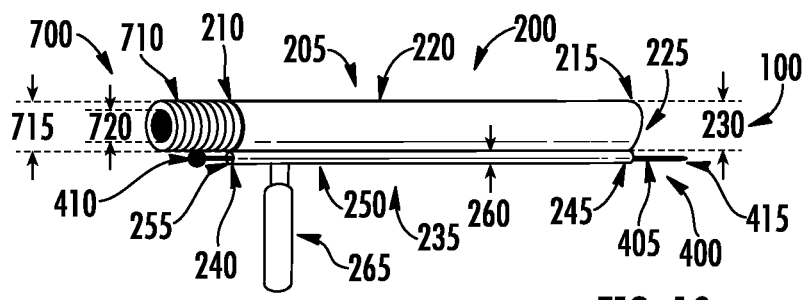
FIG. 10 is another perspective view of an example MIS system that includes a MIS apparatus, an anchor pin, and a pedicle screw or lateral mass screw reducer.
Figure 11:
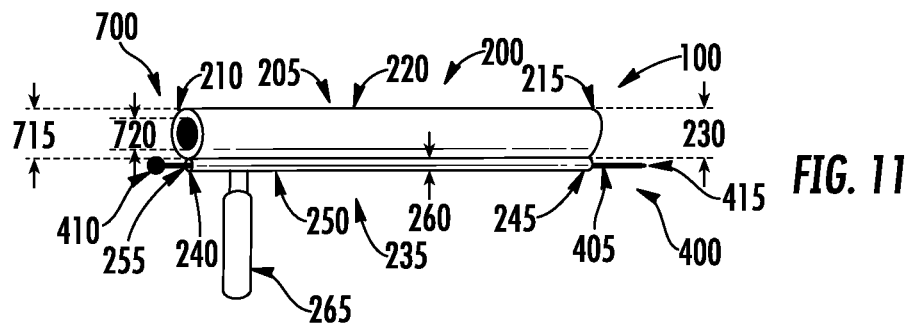
FIG. 11 is another perspective view of an example MIS system that includes a MIS apparatus, an anchor pin, and a pedicle screw or lateral mass screw reducer.

In certain embodiments, the MIS system 100 includes an anchor pin 400. As illustrated in FIG. 4, the anchor pin 400 can be inserted into the anchor pin receiving chamber 235 to anchor the MIS apparatus 200 to a vertebral lateral mass 900. In certain embodiments the anchor pin 400 includes an elongated member 405, a proximal stopping knob 410, and a proximal protruding end 415. When the anchor pin 400 is located within the anchor pin receiving chamber 235, the proximal protruding end 415 extends a distance past the second distal end. One suitable distance is about 12 millimeters. It should be understood that in certain embodiments more than one anchor pin 400 may be used in one or more anchor pin receiving chambers 235.

In certain embodiments, the MIS system 100 includes a drill guide reducer 500. As illustrated in FIGS. 5-8, the drill guide reducer 500 can be inserted into the instrument portal 205 of the MIS apparatus 200 to accommodate a diameter 605 of a drill guide 600 used to drill a hole into a vertebral lateral mass 900. In certain embodiments the drill guide reducer 500 includes an elongated cylindrical member 510 having an outer diameter 515 sized to fit within the instrument portal 205 and an inner diameter 520 sized to fit the diameter 605 of the drill guide 600. In certain embodiments, the diameter 605 of the drill guide 600 is smaller than the first diameter 230. In certain embodiments, the inner diameter 520 of the drill guide reducer 500 ranges from about 1.75 millimeters to about 3.25 millimeters. In certain embodiments, the inner diameter 520 of the drill guide reducer 500 is about 3 millimeters. In certain embodiments, a surface of the elongated member 510 can include threads, grips, or other means for creating a friction fit between the elongated member 510 and the first cylindrical bore 225.

In certain embodiments, the MIS system 100 includes a pedicle screw or lateral mass screw reducer 700. As illustrated in FIGS. 9-17, the pedicle screw or lateral mass screw reducer 700 can be inserted into the instrument portal 205 of the MIS apparatus 200 to accommodate a diameter of a head of the pedicle screw or lateral mass screw 800. In certain embodiments, the pedicle screw or lateral mass screw reducer 700 includes an elongate cylindrical member 710 having an outer diameter 715 sized to fit within the instrument portal 205 and an inner diameter 720 sized to fit the diameter of the pedicle screw or lateral mass screw head. The diameter of the head of the pedicle screw or lateral mass screw is smaller than the first diameter. In certain embodiments, the inner diameter 720 of the pedicle screw or lateral mass screw reducer 700 ranges from about 7 millimeters to about 12 millimeters. In certain embodiments a surface of the elongated member 710 can include threads, grips, or other means for creating a friction fit between the elongated member 710 and the first cylindrical bore 225.

Although the MIS system 100 is described as including a MIS apparatus 200 and one or more of the above devices (e.g., inner cannula 300, anchor pin 400, drill guide reducer 500, drill guide 500, pedicle scree reducer 700, etc.), it should be understood that the MIS apparatus 200 can be described as further comprising within itself one or more of the various other devices at different points in time. For example, in one embodiment the MIS apparatus 200 may include an instrument portal 205, a pedicle screw or lateral mass screw reducer 700 located within the instrument portal 205, an anchor pin receiving chamber 235 fixed in parallel to the instrument portal 205, an anchoring pin 400 located within the anchor pin receiving chamber 235, and a handle 265 depending from a surface of the instrument portal 205 or a surface of the anchor pin receiving chamber 235.

Figure 12:
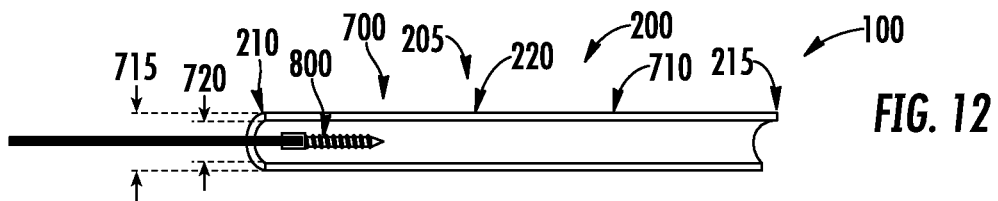
FIG. 12 is a partial cutaway view of the system of FIG. 11, wherein the view shows a pedicle screw or lateral mass screw being inserted into the MIS apparatus.
Figure 13:
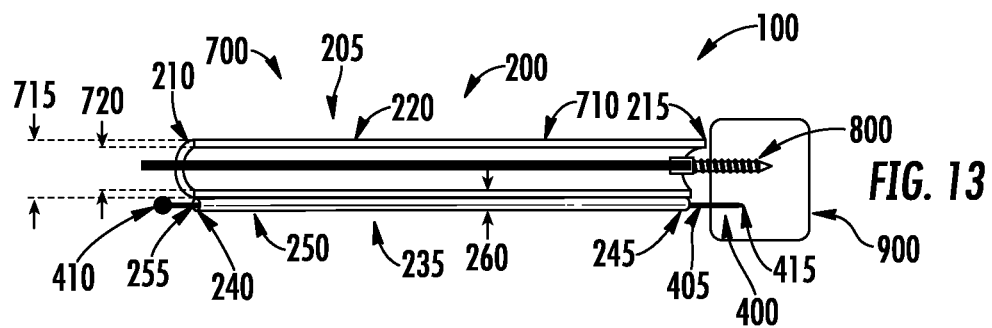
FIG. 13 is another partial cutaway view of the system of FIG. 11, wherein the view shows a pedicle screw or lateral mass screw being screwed into a lateral vertebral mass.
Figure 14:
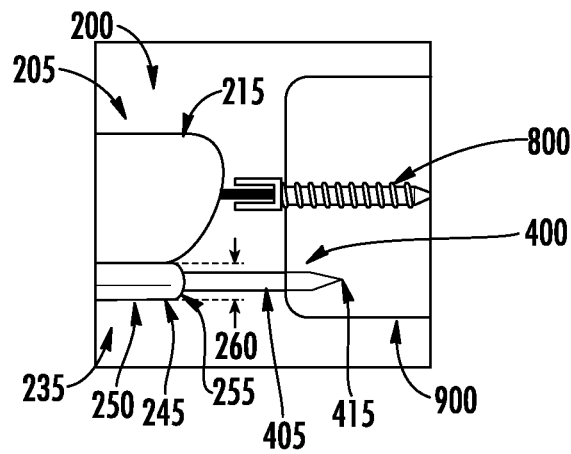
FIG. 14 is an exploded view of the system of FIG. 11, wherein the view shows a pedicle screw or lateral mass screw being screwed into a lateral vertebral mass.
Figure 15:
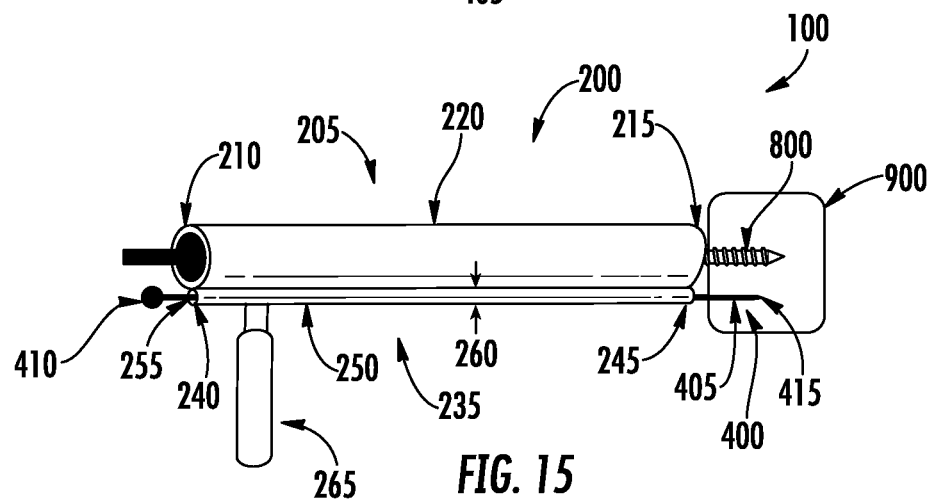
FIG. 15 is a perspective view of the system of FIG. 11, wherein the view shows a pedicle screw or lateral mass screw being screwed into a lateral vertebral mass.
Figure 16:
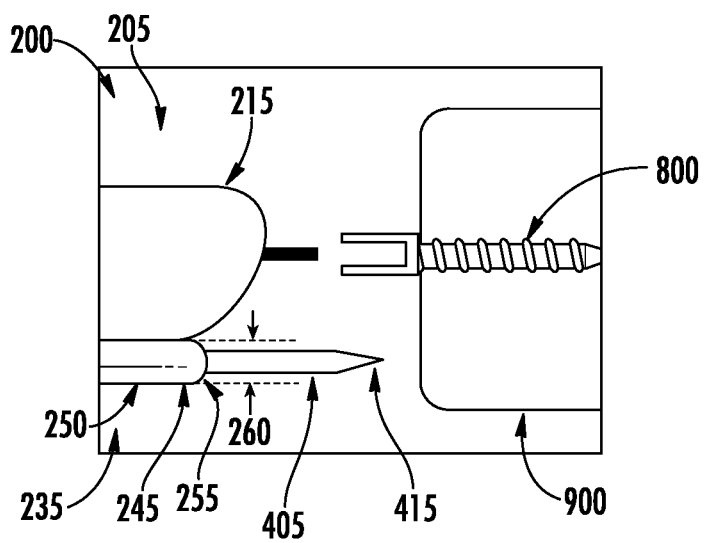
FIG. 16 is an exploded view of the system of FIG. 11, wherein the view shows a MIS apparatus being withdrawn from a lateral vertebral mass.

Also provided are methods for securing a pedicle screw or lateral mass screw 800 to a vertebral lateral mass 900 using a MIS system like the MIS system 100 shown in FIGS. 1-16. In one example, the method includes providing a MIS apparatus 200 that includes an instrument portal 205, an anchor pin receiving chamber 235 and a handle 265 as described in detail above. The example method further includes inserting a pedicle screw or lateral mass screw 800 into the instrument portal 205 and then screwing the pedicle screw or lateral mass screw 800 into a vertebral lateral mass 900 via the instrument portal 205. In certain embodiments, the method includes performing one or more of the steps recited below prior to the insertion of the pedicle screw or lateral mass screw 800. For example, the method can further include inserting an inner cannula 300 into the instrument portal 205 and then advancing the MIS apparatus 200 toward the vertebral lateral mass 900, an example of which can be seen in the transition from FIG. 2 to FIG. 3. The method can further include, anchoring the MIS apparatus 200 to the vertebral mass 900 by inserting an anchor pin 400 through the anchor pin receiving chamber 235 into the vertebral lateral mass 900, and then removing the inner cannula 300 from the MIS apparatus 200, an example of which can be seen in FIG. 4. The method can further include inserting a drill guide reducer 500 into the instrument portal 205 to accommodate a diameter of a drill guide 600 used to drill a hole into the vertebral lateral mass or pedicle 900, an example of which can be seen in the transition from FIG. 5 to FIG. 7. The method can further include inserting the drill guide 600 into the drill guide reducer 500 to drill the hole in the vertebral lateral mass or pedicle 900, an example of which can be seen in FIG. 8, and then removing the drill guide 600 and the drill guide reducer 500 from the MIS apparatus 200. The method can further include inserting a pedicle screw or lateral mass screw reducer 700 into the instrument portal 205 to accommodate a diameter of a head of the pedicle screw or lateral mass screw 800, an example of which can be seen in the transition from FIG. 9 to FIG. 11. In certain embodiments the step of inserting of the pedicle screw or lateral mass screw 800 into the instrument portal 205 includes inserting the pedicle screw or lateral mass screw 800 into the pedicle screw or lateral mass screw reducer 700 as shown in FIG. 12. In certain embodiments the step of screwing the pedicle screw or lateral mass screw 800 into the vertebral lateral mass or pedicle 900 includes screwing the pedicle screw or lateral mass screw 800 into the hole of the vertebral lateral mass or pedicle 900 through the pedicle screw or lateral mass screw reducer 700, an example of which is shown in the transition from FIG. 13 to FIG. 15. The method can further include removing the anchor pin 400 from the anchor pin receiving chamber 235 and withdrawing the MIS apparatus 200 away from the vertebral lateral mass or pedicle 900, an example of which is shown in FIG. 16.

The MIS apparatus 200 and the various components described above can be created from various types of suitable materials, for example, biocompatible materials like titanium and polyethylene ketone. The parts can be created through 3D printing and/or through other processes that are known to those having ordinary skill in the art.

A number of embodiments of the invention have been described. Nevertheless, it will be understood that various modifications may be made without departing from the spirit and scope of the invention. Accordingly, other embodiments are within the scope of the following claims.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a method is disclosed and discussed each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

The invention claimed is:

1. A surgical system comprising:
an instrument portal comprising a first proximal end, a first distal end, and a first elongated member, the first elongated member defining a first bore having a first diameter, wherein the first bore extends from the first distal end to the first proximal end, wherein the maximum clearance of the instrument portal is the first diameter;

a drill guide reducer configured to be inserted into the instrument portal, the drill guide reducer comprising an elongated cylindrical member defining an outside diameter that is smaller than the first diameter, such that the drill guide reducer is sized to fit within the instrument portal and defining an inner diameter configured to receive a drill guide, wherein the inner diameter of the drill guide reducer is smaller than the first diameter of the instrument portal;

an anchor pin receiving chamber positioned outside of the first elongated member and fixed in parallel to the instrument portal comprising a second proximal end, a second distal end, and a second elongated member comprising a second bore, the second bore defining a second diameter, wherein the second bore extends from the second distal end to the second proximal end, and wherein the second diameter is smaller than the first diameter; and an anchor pin to be inserted into the anchor pin receiving chamber for anchoring the system to a vertebral lateral mass or a pedicle, the anchor pin comprising an elongated member, a proximal stopping knob, and a proximal protruding end, wherein a distal protruding end extends past the second distal end when the anchor pin is located within the anchor pin receiving chamber.

2. The system of claim 1, further comprising:
an inner cannula to be inserted into the instrument portal for advancing the MIS apparatus toward a vertebral lateral mass or a pedicle, the inner cannula comprising a proximal end, a distal end, and an elongated member defining an outer diameter sized to fit within the instrument portal.

3. The system of claim 2, wherein the distal end of the inner cannula is tapered.

4. The system of claim 2, wherein the inner cannula is radiopaque.

5. The system of claim 2, wherein the inner cannula is sized to fit against an inner surface of the instrument portal.

6. The system of claim 1 further comprising:
a screw reducer to be inserted into the instrument portal to accommodate a head of a screw, the screw reducer comprising an elongated cylindrical member sized to fit within the instrument portal and an inner opening sized to fit the head of the screw, wherein the head of the screw defines an outer diameter that is smaller than the first diameter.

7. The system of claim 1, wherein the instrument portal is radiolucent.

8. The system of claim 1, wherein the first distal end includes an oblique end contoured to fit against a vertebral lateral mass or a pedicle.

9. A surgical apparatus comprising:
an instrument portal comprising a first proximal end, a first distal end, and a first elongated member, the first elongated member comprising a first cylindrical bore defining a first diameter, wherein the first cylindrical bore extends from the first distal end to the first proximal end, wherein the maximum clearance of the instrument portal is the first diameter;

a screw reducer located within the instrument portal to accommodate a head of a screw, the screw reducer comprising an elongated cylindrical member sized to fit within the instrument portal and an opening defining an inner diameter sized to fit the head of the screw, wherein the head of the screw defines a diameter that is smaller than the first diameter;

an anchor pin receiving chamber positioned adjacent the first elongated member and fixed in parallel to the instrument portal;

a drill guide reducer configured to be inserted into the instrument portal, the drill guide reducer comprising an elongated cylindrical member defining an outside diameter such that the drill guide reducer is sized to fit within the instrument portal and defining an inner diameter configured to receive a drill guide, wherein the inner diameter of the drill guide reducer is less than the first diameter; and an anchor pin located within the anchor pin receiving chamber for anchoring the apparatus to the vertebral lateral mass or a pedicle, the anchor pin comprising an elongated member, a proximal stopping knob, and a proximal protruding end, wherein the proximal protruding end extends past the second distal end to engage the vertebral lateral mass or a pedicle.

10. The apparatus of claim 9, wherein the instrument portal is radiolucent.

11. The apparatus of claim 9, wherein the first distal end includes an oblique end contoured to fit against a vertebral lateral mass or a pedicle.

12. The apparatus of claim 9, wherein the drill guide reducer reduces the maximum clearance of the instrument portal.

13. The apparatus of claim 9, wherein the instrument portal comprises a second proximal end, a second distal end, and a second elongated member, the second elongated member comprising a second cylindrical bore defining a second diameter, wherein the second cylindrical bore extends from the second distal end to the second proximal end, and wherein the second diameter is smaller than the first diameter.

14. The apparatus of claim 9, further a handle coupled to at least one of an outer surface of the instrument portal or an outer surface of the anchor pin receiving chamber.

* * * * *